US009927538B2

(12) United States Patent
Bordy

(10) Patent No.: US 9,927,538 B2
(45) Date of Patent: Mar. 27, 2018

(54) METHOD OF PRODUCING A RADIOMETRIC PHYSICAL PHANTOM OF A BIOLOGICAL ORGANISM AND PHYSICAL PHANTOM PRODUCED BY THIS METHOD

(71) Applicant: COMMISSARIAT A L'ENERGIE ATOMIQUE ET AUX ENERGIES ALTERNATIVES, Paris (FR)

(72) Inventor: Jean-Marc Bordy, Savigny sur Orge (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/320,274

(22) PCT Filed: Jun. 23, 2015

(86) PCT No.: PCT/EP2015/064126
§ 371 (c)(1),
(2) Date: Dec. 19, 2016

(87) PCT Pub. No.: WO2015/197625
PCT Pub. Date: Dec. 30, 2015

(65) Prior Publication Data
US 2017/0248708 A1    Aug. 31, 2017

(30) Foreign Application Priority Data
Jun. 25, 2014   (FR) ...................................... 14 55911

(51) Int. Cl.
*G01T 7/00*      (2006.01)
*B29C 67/00*     (2017.01)
(Continued)

(52) U.S. Cl.
CPC .......... *G01T 7/005* (2013.01); *B29C 67/0055* (2013.01); *B29C 67/0088* (2013.01);
(Continued)

(58) Field of Classification Search
CPC ............ B29C 67/0055; B29C 67/0088; B29K 2105/0061; B29L 2031/40; B33Y 10/00;
(Continued)

(56) References Cited
U.S. PATENT DOCUMENTS
2005/0077459 A1    4/2005  Engler et al.
2010/0047752 A1*   2/2010  Chan ................... B29C 33/3857
                                                       434/272
(Continued)

FOREIGN PATENT DOCUMENTS
KR         10-1378875 B1      3/2014

OTHER PUBLICATIONS
Baldock, C., et al., "Topical Review: Polymer Gel Dosimetry," Physics in Medicine and Biology 55(5):R1-R63, Mar. 2010.
(Continued)

*Primary Examiner* — Mark R Gaworecki
(74) *Attorney, Agent, or Firm* — Christensen O'Connor Johnson Kindness PLLC

(57) ABSTRACT

A method of producing a radiometric physical phantom of a biological organism to be irradiated or already irradiated having at least two volumes of appreciably different biological tissues comprises a step of determining a radiological three-dimensional model on the basis of anatomical three-dimensional image(s) of the organism, a step of producing a material framework of the phantom with the aid of a 3D printer, and a step of filling the enclosures of the framework with gels.

18 Claims, 4 Drawing Sheets

(51) Int. Cl.
    *B33Y 10/00*     (2015.01)
    *B33Y 30/00*     (2015.01)
    *B33Y 50/02*     (2015.01)
    *B33Y 80/00*     (2015.01)
    *B29K 105/00*    (2006.01)
    *B29L 31/40*     (2006.01)
(52) U.S. Cl.
    CPC ............... *B33Y 10/00* (2014.12); *B33Y 30/00* (2014.12); *B33Y 50/02* (2014.12); *B33Y 80/00* (2014.12); *B29K 2105/0061* (2013.01); *B29L 2031/40* (2013.01)
(58) Field of Classification Search
    CPC ......... B33Y 30/00; B33Y 50/02; B33Y 80/00; G01T 7/005
    See application file for complete search history.

(56) References Cited

U.S. PATENT DOCUMENTS

| | | | | |
|---|---|---|---|---|
| 2010/0202001 | A1* | 8/2010 | Miller | A61B 6/583 358/1.9 |
| 2016/0148541 | A1* | 5/2016 | Ristolainen | G09B 23/285 434/268 |

OTHER PUBLICATIONS

Gallas, R.R., et al., "An Anthropomorphic Multimodality (CT/MRI) Phantom Prototype for End-to-End Tests in Radiation Therapy," arXiv preprint arXiv:1402.3793, Feb. 2014, pp. 1-22.

International Search Report dated Sep. 14, 2015, issued in corresponding International Application No. PCT/EP2015/064126, filed Jun. 23, 2015, 3 pages.

Rengier, F., et al., "3D Printing Based on Imaging Data: Review of Medical Applications," International Journal of Computer Assisted Radiology and Surgery 5(4):335-341, May 2010.

Besbes, M., et al., "Study of in Vivo Dosimetry by EPD-20 Semiconductors Under the Conditions of Total Body Irradiation," Cancer Radiothérapie, 14(1):29-33, Jan. 1, 2010.

Bottollier-Depois, J.F., et al., "Physical Dosimetry Techniques for the Reconstruction of Radio Accidents," Journal de Chimie Physique et de Physico-Chimie Biologique 95(4): 685-690, Apr. 1, 1998.

Bouche, E., et al., "Guide for Everyday Practice of the Dosimetry in Vivo in External Radiotherapy," Institut National du Cancer (INCa), Societe Française de Physique Medicale (SFPM) and Autorite de Surete Nucleaire (ASN) Oct. 2008 <http://documents.sfpm.fr/docs_sfpm/200810_guide_dosi_in_vivo.pdf> [retrieved Oct. 17, 2017], 86 pages (including English translation).

Schreiner, L.J., "Review of Fricke Gel Dosimeters", Journal of Physics: Conference Series 3, pp. 9-21, Sep. 2004.

Van Zijtveld, M. et al., "3D Dose Reconstruction for Clinical Evaluation of IMRT Pretreatment Verification With an EPID," Radiotherapy and Oncology 82:201-207, Feb. 2007.

Written Opinion of the International Searching Authority dated Sep. 14, 2015, issued in corresponding International Application No. PCT/EP2015/064126, filed Jun. 23, 2015, 10 pages.

International Preliminary Report of Patentability dated Dec. 27, 2016, issued in corresponding International Application No. PCT/EP2015/064126, filed Jun. 23, 2015, 1 page.

* cited by examiner

METHOD OF PRODUCING A RADIOMETRIC PHYSICAL PHANTOM OF A BIOLOGICAL ORGANISM AND PHYSICAL PHANTOM PRODUCED BY THIS METHOD

The present invention concerns a method to produce a radiometric physical phantom representing a biological organism for the precise, experimental determination of the three-dimensional distribution of radiation doses received or to be received by the organism.

The present invention also concerns a radiometric physical phantom produced by the method and a system to implement the method for producing the phantom.

The present invention further concerns a method for the experimental determination of the three-dimensional distribution of real radiation doses received or to be received by the biological organism by means of said physical phantom.

When external radiotherapeutic treatment is administered to a patient, the radiation doses received must be verified, or when a radiological accident occurs the reconstitution data of the accident must be validated.

At the present time, the verification of external radiotherapy treatment is compulsory and conducted via in vivo dosimetry following laid down rules, for example those described in the document titled « Guide pour la pratique quotidienne de la Dosimétrie in Vivo en radiothéerapie externe», multi-authored by E. Bouche et al., under the aegis of the French national cancer institute Institut National du Cancer (INCa) with the collaboration of Société Française de Physique Médicale (SFPM) and the nuclear safety body l'Autorité de Sureté Nucléaire.

In vivo dosimetry is performed using dosimeters which may have deferred reading such as thermo-luminescent dosimeters, or instantaneous reading such as electronic diode dosimeters, positioned on the skin during treatment.

In vivo dosimetry performed using electronic diode dosimeters is described for example in the article on in vivo dosimetry under full body radiation conditions using EPD-20 semiconductors by M. Besbes et al., titled « Étude de la dosimétrie in vivo par semi-conducteurs EPD-20 dans les conditions de l'irradiation corporelle totale», published in Cancer Radiothérapie vol. 14—no 1-January 2010 pp 29-33.

In vivo dosimetry may also be performed using two-dimensional images obtained using an Electronic Portal Imaging Device (EPID).

In both implementations of in vivo dosimetry, verification of the radiation doses received is partial, sometimes performed a posteriori in particular when using dosimeters with deferred reading since they do not give access to information on three-dimensional distribution (3D) of the doses received inside the patient's body unless reconstruction software is used as described in the article by Mathilda van Zijtveld et al. « 3D dose reconstruction for clinical evaluation of IMRT pretreatment verification with an EPID», published in Radiotherapy and Oncology 82 (2007), pages 201-207.

If a radiological accident occurs, the search for exposure conditions is carried out using reconstitution software as described in the article on physical dosimetry techniques by J. F. Bottollier-Depois et al: « Techniques de dosimétrie physique pour la reconstitution d'accident radiologique», published in J. Chim. Phys., Volume 95, Number 4, April 1998, pp. 685-690.

This type of software, using geometric data describing the location of the accident incorporates therein a standard digital anthropomorphic phantom.

As in the preceding case, the distribution of doses in the phantom is not truly representative of the patient since the morphology of the patients differs from the morphology of the phantom used. In addition, reconstitution software must be experimentally validated.

In both the above-described cases, another solution is to irradiate standard real physical phantoms under the same conditions as the patient, these phantoms being more or less anthropomorphic and inside which a large number of point dosimeters have been arranged. The measurement of each of these dosimeters allows the three-dimensional reconstruction of a map of the radiation doses received in the phantom However, even in this case, the distribution of doses in the phantom is not truly representative of the patient since the particular morphology of the patient differs from the standard morphology of the phantoms used and the 3D reconstitution is obtained within « geometry» that is removed from the anthropomorphic reality of the patient.

The technical problem is to improve the accuracy of methods to verify and validate external radiotherapy treatment planning and/or reconstitution computing of radiological accidents in terms of consideration given to the particular anatomy of each body when a physical phantom is used.

The technical problem is to have access to the three-dimensional distribution of radiation doses received inside a realistic anthropomorphic phantom of an organism, whether or not human, which takes the anatomical particularities thereof into account.

The technical problem is to produce a customized radiometric physical phantom representing patients in their differences with other patients of the same biological species.

For this purpose, the subject of the invention is a method to produce a radiometric physical phantom of a biological organism for the experimental determination under predetermined radiation conditions of the volume distribution of radiation doses received by the phantom, representing the dose distribution which would be received by the biological organism placed under the same irradiating conditions, the biological organism having at least two volumes of biological tissues with distinctly different chemical compositions and densities, the production method comprising the steps of:

from one or more three-dimensional anatomical images of the tissues in terms of chemical compositions and densities, determining a three-dimensional radiological model representing radiation absorption and diffusion inside the biological organism, by grouping together in radiological organs tissues that are adjacent and have close chemical compositions and densities, each radiological organ geometrically occupying a radiological volume in space equal to, or close to via smoothing of its enveloping contours, the sum of the volumes of all the tissues grouped together in the same radiological organ, and being characterized by a radiological class identifying the range of close chemical compositions and densities grouped together within the same radiological organ; then using the radiological model, and by means of 3D printing, forming a material frame of the physical phantom by reproducing each radiological volume as a chamber filled with air and delimited by a wall, the wall being formed of 3D printing ink; then filling each chamber of the material frame of the phantom, associated with a radiological organ, with dosimetric gel having physical characteristics close to or identical to those of the class of chemical compositions and densities of the radiological organ.

According to particular embodiments, the method to produce a radiometric physical phantom comprises one or more of the following characteristics taken alone or in combination:

when determining the radiological model:
for each group of biological tissues in one same radiological organ,
an intermediate radiological volume is first determined as being equal to the sum of the volumes of the tissues grouped together in the radiological organ, then
the radiological volume of the radiological organ is determined by smoothing the contours of the intermediate radiological volume to limit anfractuosities and to facilitate filling with the dosimetric gel;
the method to produce a radiometric physical phantom also comprises a step to prepare software plans to produce the material frame of the phantom and to translate these plans into a 3D print control programme of the frame, inserted between the step to determine the radiological model and the 3D printing step of the phantom frame, and during this preparation step
for each chamber associated with a radiological organ, the number of gel inlet filling orifices, the number of air filling and outlet orifices, the positions and diameters of the gel inlet filling orifice(s) and of the air filling and outlet orifice(s), and the pathways and diameters of the chamber filling ducts connected between the filling orifices and the outside of the phantom are determined so as to:
allow filling of the radiological organ without any volume bubbles;
the total number of filling orifices, the positions of the filling orifices and the pathways of the filling ducts of all the chambers are determined so as not to hamper propagation of radiation towards a region to be treated as a function of the location of the region to be treated and/or of the entry angle of the radiation beam;
the total number of filling orifices, the positions of the filling orifices and the pathways of the filling ducts, the smoothed forms of the chamber volumes are determined so as not to hamper propagation of radiation towards the region to be treated as a function of the location of the region to be treated and/or of the entry angle of the radiation beam;
the dosimetric gels are included in the group formed by Fricke gels and polymer gels.

A further subject of the invention is a method for experimental determination of the volume distribution of radiation doses received by a radiometric physical phantom representing the dose distribution which would be received by the part or all of a biological organism placed under the same predetermined irradiating conditions, comprising the steps of:

providing a physical phantom filled with its dosimetric gels and produced according to the above-defined method;
irradiating the physical phantom under the predetermined irradiating conditions;
reading a physical parameter of the gels in situ in the phantom by placing the phantom filled with irradiated gels in imaging apparatus, for example using an optical transmission method or in NMR imaging apparatus, and encoding the parameter in the form of raw read-out data;
processing the raw read-out data to determine an image of the three-dimensional distribution of the radiation doses received in the part or all of the biological organism.

Depending on particular embodiments, the method for experimental determination of the volume distribution of radiation doses received by a phantom comprises one or more of the following characteristics taken alone or in combination:

the raw read-out data represent a read-out physical parameter included in the group formed by optical density, relaxation time;
the processing step of read-out data comprises the steps of:
translating the raw read-out data into terms of absorbed doses; and
grouping together the data translated into terms of absorbed doses to create particular images included in the group formed by two-dimensional sections along a predetermined sectional plane, three-dimensional « isodose » surfaces, images proposed by radiotherapy treatment planning software;
the radiation is radiation of particles included in the group formed by photons, electrons, protons, heavy nuclei.

A further subject of the invention is a radiometric physical phantom of a biological organism for the experimental determination, under predetermined irradiating conditions, of the volume distribution of radiation doses received by the phantom representing the dose distribution which would be received by the biological organism placed under the same irradiating conditions, the biological organism having at least two volumes of biological tissues with chemical compositions and densities that are distinctly different, characterized in that the physical phantom comprises:

at least two chambers held in position within a supporting frame, delimited by respective walls formed of solid 3D printing ink transparent to radiation, and each filled with a different dosimetric gel,
the at least two chambers having different and separate radiological volumes, each radiological volume being identical to, or close to via contour smoothing, the sum of the volumes of a complete group of grouped biological tissues of the radiologically-imitated biological organism, said grouped tissues being adjacent and having close chemical compositions and densities, and
the at least two dosimetric gels, each filling at least one different chamber, each having physical characteristics close to the chemical compositions and densities of the grouped adjacent biological tissues, the sum of their volumes being identical, or close to via smoothing, to the radiological volume of the chamber that is filled with the gel.

In accordance with different embodiments, the radiometric physical phantom comprises one of more of the following characteristics taken alone or in combination:

each chamber comprises at least one gel inlet filling orifice and at least one air filling and outlet orifice, and at least two filling ducts connected between the filling orifices and the outside of the phantom, and
for each chamber, the number of gel inlet filling orifices, the number of air filling and outlet orifices, the positions and the diameters of the gel inlet filling orifice(s) and air filling and outlet orifices(s), and the pathways and diameters of the chamber filling ducts connected between the filling orifices and the outside of the phantom are configured to allow filling of the chamber at a predetermined rate without creating any volume bubbles.

A further subject of the invention is a system to produce a radiometric physical phantom simulating the radiation absorption or diffusion properties of a biological organism, the biological organism having at least two volumes of biological tissues having distinctly differing chemical compositions and densities,
the system comprising:

means for providing one or more three-dimensional anatomic images of the tissues in terms of chemical composition and density, an electronic computer configured to:

on the basis of one of more three-dimensional anatomic images of the tissues in terms of chemical composition and density, determine a three-dimensional radiological model representing radiation absorption and diffusion inside the biological organism, by grouping together within radiological organs those tissues that are adjacent and have close chemical compositions and densities, each radiological organ geometrically occupying in space a radiological volume equal to, or close to via smoothing of its enveloping contours, the sum of the volumes of all the tissues grouped together within the same radiological organ, and being characterized by a radiological class identifying the range of close chemical compositions and densities of the tissues grouped together within the same radiological organ, and using the three-dimensional radiological model, to determine the plans of a material frame of the phantom in the form of a set of chambers, gel filling ducts into the chambers, and supporting elements to hold the chambers in position together, then to translate the material frame plans into a 3D print control programme to be executed by a predetermined 3D printer, the predetermined 3D printer being configured to produce the material frame of the phantom before filling with dosimetric gels, using radiation-transparent 3D printing inks;

at least two different dosimetric gels, each intended to fill a different radiological chamber associated with a different radiological organ in terms of class of chemical compositions and densities, and means for filling the empty phantom with the at least two dosimetric gels.

According to different particular embodiments, the system to produce a radiometric physical phantom comprises one or more of the following characteristics taken alone or in combination:

the electronic computer, for each group of biological tissues within a radiological organ, is configured:

to determine an intermediate radiological volume as being equal to the sum of the volumes of the tissues grouped together within the radiological organ, and to determine the radiological volume of the radiological organ by smoothing the contours of the intermediate radiological volume to limit anfractuosities and to facilitate future filling with gel;

the electronic computer, for each radiological organ, is configured:

to determine the number of gel inlet filling orifices, the number of air filling and outlet orifices, each position and diameter of the gel inlet filling orifice(s), each position and diameter of the air filing and outlet orifice(s), and the pathways and diameters of the filling ducts of the radiological organ volumes, connected between the filling orifices and the outside of the phantom, so as to:

allow filling of the radiological organ without any volume bubbles;

the electronic computer is configured to determine the total number of filling orifices, the positions of the filling orifices and the pathways of the filling ducts so that the ducts do not hamper propagation of radiation towards a region to be treated as a function of the location of the region to be treated, and of the entry angle of the radiation beam;

the electronic computer is configured to determine the total number of filling orifices, the positions of the filling orifices and the pathways of the filling ducts, the smoothed forms of the radiological organ volumes so as to avoid signification modification of propagation of radiation towards a region to be treated as a function of the location of the region to be treated, and of the entry angle of the radiation beam.

A further subject of the invention is a system for the experimental determination of the volume distribution of radiation doses received by a phantom representing a dose distribution which would be received by the part or all of the biological organism placed under the same predetermined irradiating conditions, comprising:

a system to produce a radiometric physical phantom filled with dosimetric gels as defined above;

means to irradiate the physical phantom with radiation under predetermined irradiating conditions;

means to read a physical parameter of the gels in situ in the phantom when the latter is filled with irradiated gels and placed in imaging apparatus using an optical transmission method for example, or in NMR imaging apparatus, and means for encoding the read-out physical parameter in the form of raw read-out data;

means for processing the raw read-out data to determine an image of the three-dimensional distribution of the radiation doses received in the biological organism.

A further subject of the invention is a computer programme product comprising a set of instructions which, when loaded and executed by the electronic computer and/or the means for processing the raw read-out data of the above-defined production system and experimental determination system, perform part of the steps of the production method defined above and in the experimental determination method defined above.

The invention will be better understood on reading the following description of several embodiments given solely as examples with reference to the drawings in which.

Figure 1:
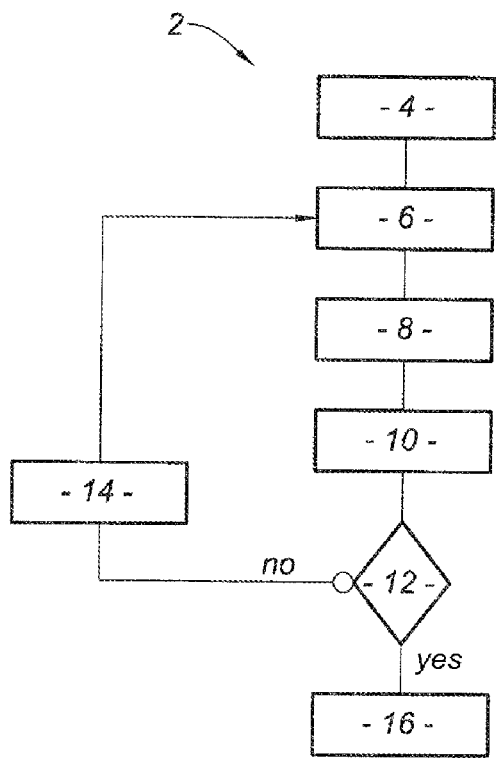
FIG. 1 is a flowchart of one embodiment of a method to produce a radiometric physical phantom of the invention.
Figure 2:
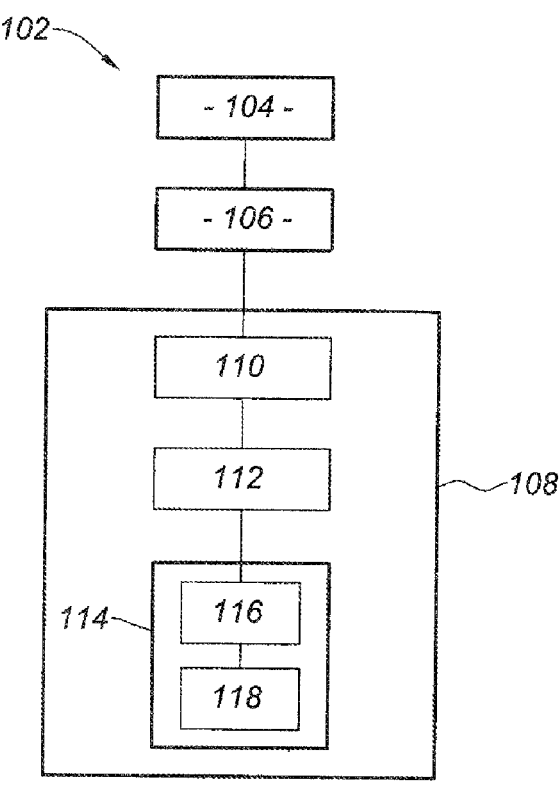
FIG. 2 is a flowchart of one embodiment of the experimental determination of the volume distribution of radiation doses received by a physical phantom produced according to the method in FIG. 1.
Figure 3:
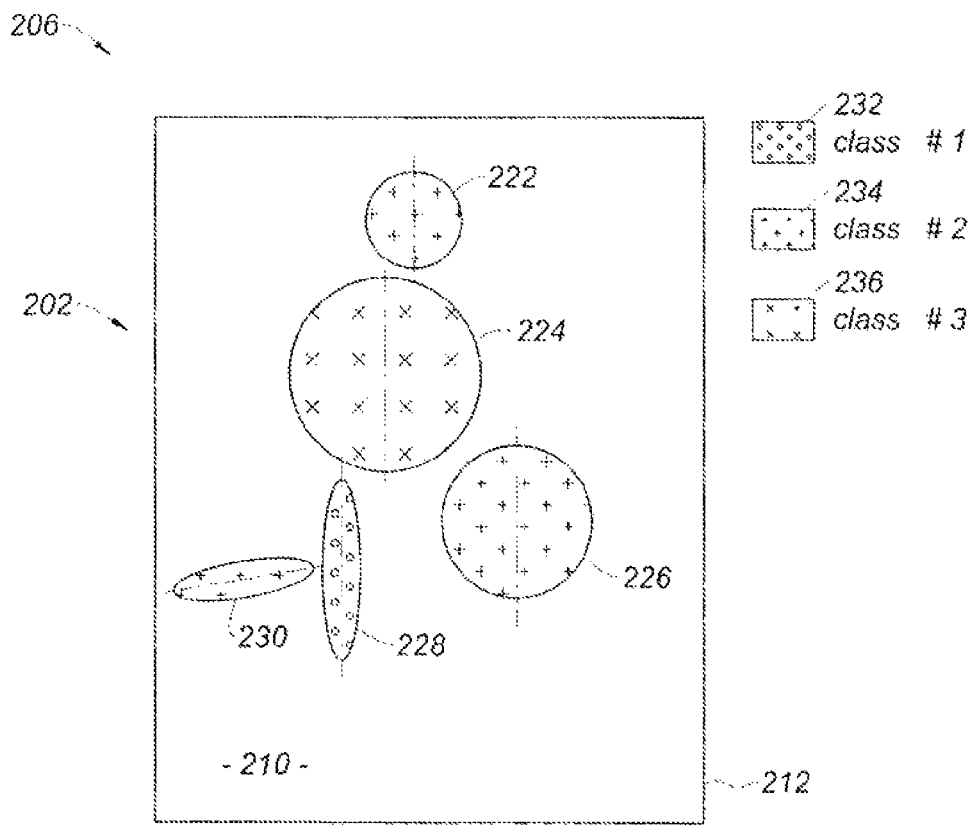
Figure 3:
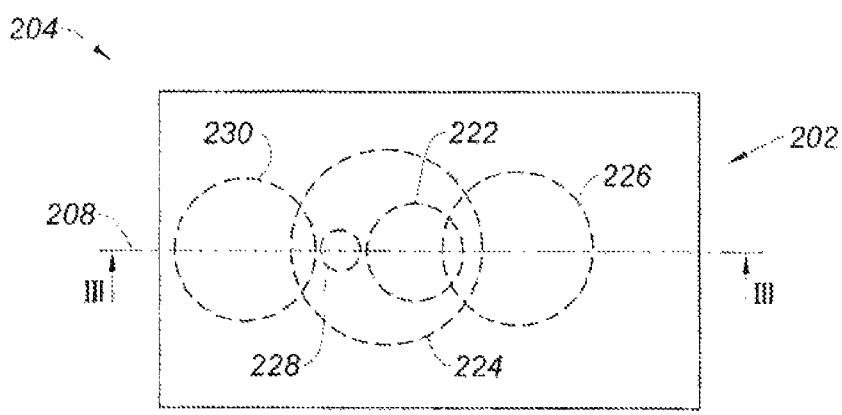
Figure 4:
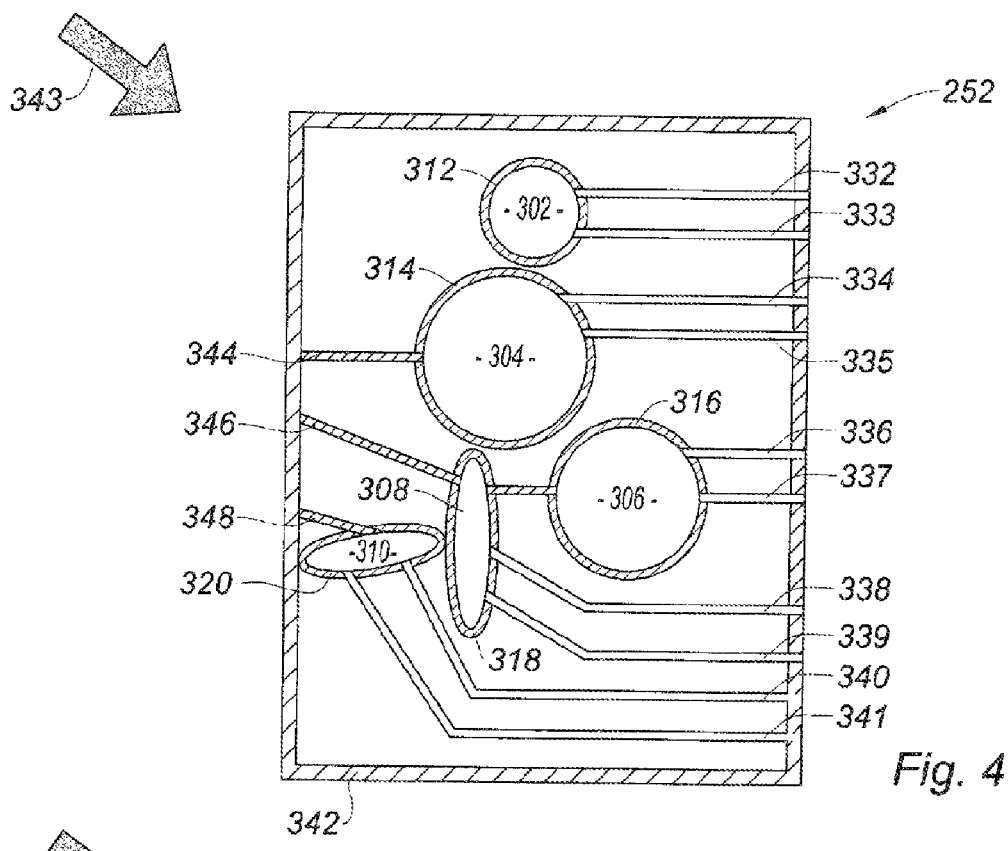
Figure 5:
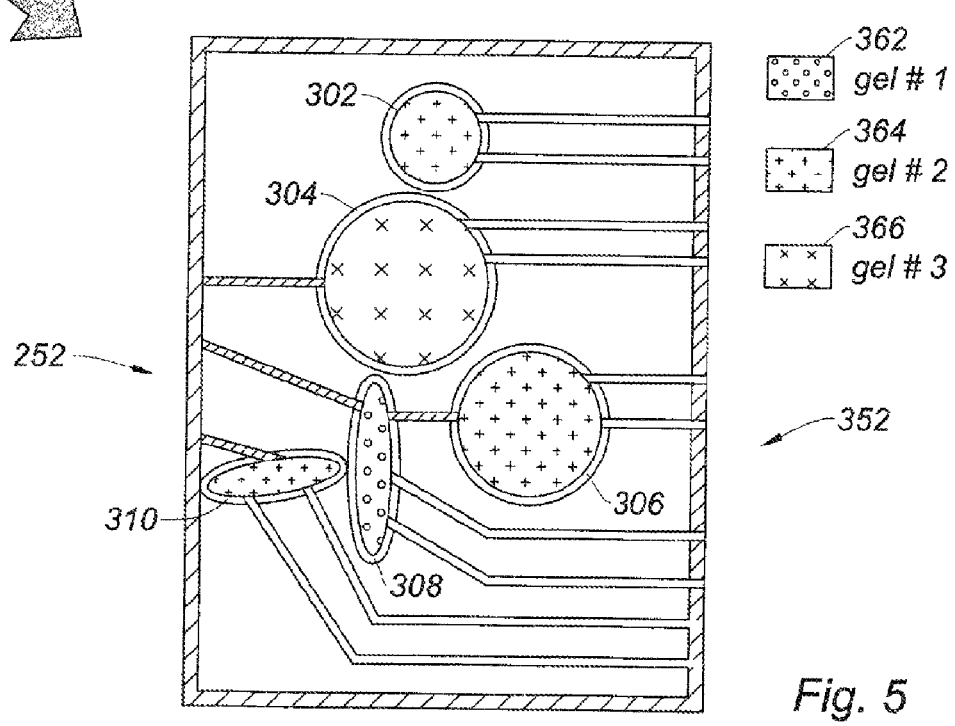
Figure 6:
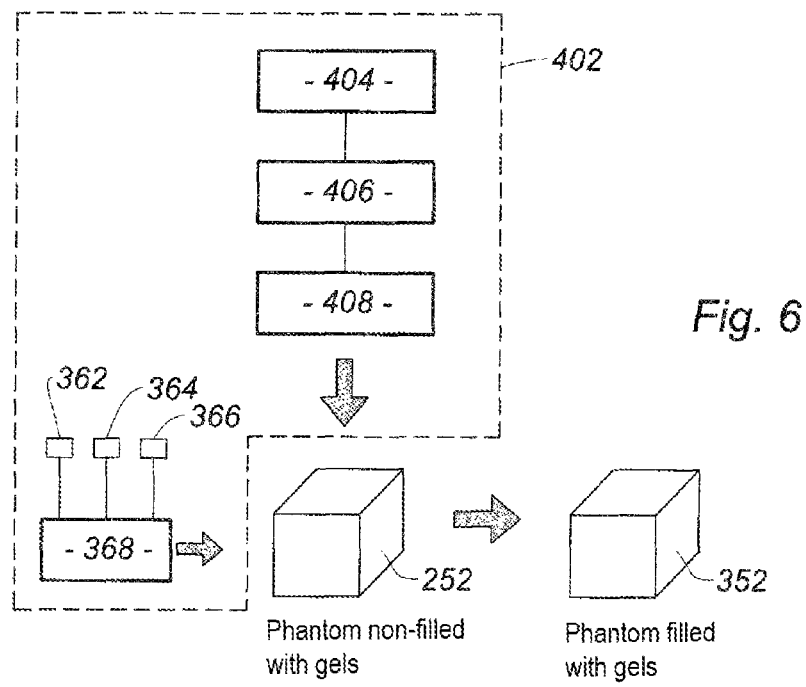
Figure 7:
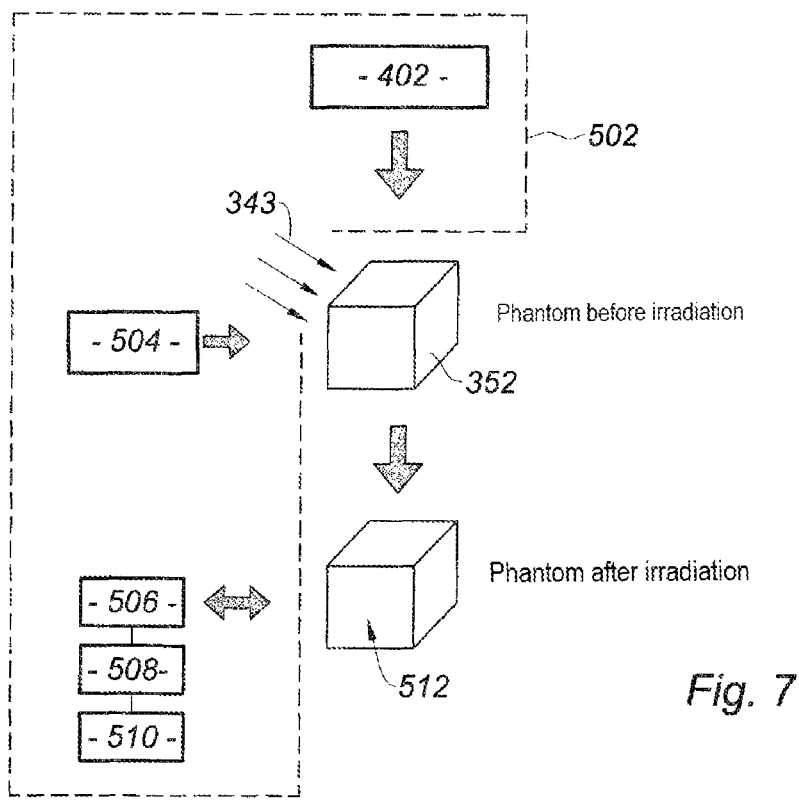

FIG. 3 first gives a global overhead view of an example of a radiological model defined in the production method of FIG. 1, and secondly a cross-section of the radiological model along a median sectional plane III-III, perpendicular to the overhead view;

FIG. 4 is a cross-sectional view along the same sectional plane as in FIG. 3 of the frame of the physical phantom obtained after the 3D printing step of the production method in FIG. 1;

FIG. 5 is a cross-sectional view of the physical phantom filled with non-irradiated dosimetric gels obtained on completion of the production method in FIG. 1, the sectional plane being identical to the plane in FIGS. 3 and 4;

FIG. 6 is a view of the architecture of a system to produce a physical phantom in FIG. 5 which implements the production method in FIG. 1;

FIG. 7 shows the architecture of a system for the experimental determination of the volume distribution of radiation doses received by the phantom in FIG. 5, produced by the production system in FIG. 6, and which implements the experimental determination method of FIG. 2.

According to FIG. 1 and one general embodiment of the invention, a method 2 to produce a radiometric physical phantom of a biological organism comprises a set of steps 4, 6, 8, 10, 12, 14 and 16.

The radiometric physical phantom is designed and prepared by method 2 for customized simulation i.e. individually and as realistically as possible, of the radiation absorption and diffusion properties of a biological organism for which its own particular anatomical characteristics are precisely known, and to allow the experimental physical determination under predetermined irradiating conditions of the volume distribution of radiation doses received, representing i.e. practically identical to the dose distribution of radiation which would be received by or may have been received by the biological organism placed under the same irradiating conditions.

The biological organism here is assumed to be sufficiently complex to have at least two different compact, separate volumes of biological tissues having chemical compositions and densities that are distinctly different e.g. bone or lung.

At the first step 4, one or more three-dimensional anatomic images of the biological tissues of the biological organism are provided. The three-dimensional anatomic image(s) represent the chemical compositions and densities of the biological tissues.

The three-dimensional anatomic image(s) are 3D diagnostic images for example representing the internal and external anatomy of a patient.

Next, at the second step 6 on the basis of the three-dimensional anatomic image(s) of the biological tissues provided at the first step 4, a three-dimensional radiological model representing radiation absorption and diffusion inside the biological organism is determined by grouping together within « radiological organs » those tissues that are adjacent and have identical or close chemical compositions and densities.

Each radiological organ is defined and characterized by a radiological organ volume and a class of close chemical compositions and densities.

The radiological organ volume of a given radiological organ is defined as a geometric volume or set of points, delimited by or contained in an enveloping surface equal, or close to via smoothing of its contours, to the sum of the geometric volumes containing all the tissues grouped together within the radiological organ.

The class of a given radiological organ designates a set of pairs each formed by a chemical composition and a mass density, and close in terms of electronic density. With each class an identification characteristic can be associated, such as a distinct range of close mass densities and electronic densities representing a tissue to be simulated.

For each group of biological tissues in a radiological organ, an intermediate radiological volume is determined as being equal to the sum of the volumes of the tissues grouped together within the radiological organ, and the radiological volume of the radiological organ is then determined by smoothing the contours of the intermediate radiological volume to limit anfractuosities and facilitate filling of a dosimetry gel representing the radiological organ.

As a variant, the step to determine the radiological model is free of any step to smooth the contours of the volume of a radiological organ.

In practice, if the biological organism is a human being, an anthropomorphic 3D radiological model as realistic as possible is made of the internal and external anatomy of the patient, using an electronic computer and software. The software performs the second step 6 by first processing the raw data of anatomical imaging to identify the different biological tissues from analysis of the grey shades in the diagnostic images, the grey shades representing the chemical composition and density of a tissue. The radiological organs are then determined by grouping together the biological tissues, and the contours of the organs are smoothed to limit anfractuosities and to facilitate subsequent filling with dosimetry gels.

Herein the term « radiological organ » is used to designate in the broadest sense all the volumes of tissues, whether or not grouped together, able to be printed by a 3D printer. The tissues concerned are those of the bones, muscles, lungs for example.

For those radiological organs not having anfractuosities, such as muscles, the smoothing is conventional to limit the total surface of the walls and thereby reduce the amount of ink material for the 3D printer used to construct the volumes of the organs. The lesser the ink material used, the lesser the perturbation of radiation propagation in relation to reality, even if the inks are selected to have radiation transparency.

One alternative is to use an ink having a composition close to that of the tissues, but even in this case to reduce printing time and the amount of materials used for economic reasons, it is better to conduct prior smoothing of the surface of the walls forming the organs.

For organs having anfractuosities, these can be « erased » or deleted to obtain a simpler representation of the organs via usual geometrical forms.

Let us take the example of the vertebrae. For example, all the vertebrae are represented by a cylinder possibly following the outline of scoliosis. The base of the cylinder may be circular, elliptical or less regular to be more realistic. The more the spine is likely to modify the propagation of radiation towards the region to be treated or investigated, the lesser the shape of the volumes can be simplified. The same reasoning applies to jaws, as the teeth can be likened to bone.

For some organs, e.g. the intestines, liver, spleen, it is not necessarily required for these to be reproduced separately as several separate radiological organs. The composition of these organs can be considered sufficiently close to allow grouped representation within one same radiological organ.

As another example, the representation of the lungs must take into account the trachea and main bronchi, but other than these it is the density of the filling gel which allows average reproduction of the « tissue-air mixture ».

The extent of realism of the internal anatomy is also dependent upon the number of different gels available so that it is possible to individualise organs considered to be close in composition.

In particular, three dosimetry gels are sufficient: a first gel for the lungs, a second gel for bone and a third gel for soft tissues. For bone, it is not necessarily required either, depending on cases, to represent those which do not interfere with radiation beams.

It is to be noted that for some bones, while it is not necessary to have detailed knowledge of dose distribution of radiation in the bone, they can be represented by solid volumes printed with « bone equivalent » ink or similar.

At the third step 8, production planning software for a material frame of the phantom is determined.

This production planning takes into account a certain number of requirements.

3D printing inks, composed of plastic materials or other gel-impermeable curable materials, can be selected for the similarity of their properties in terms of interaction with ionising radiation with those of gels and organic tissues. The selected printing inks are used to form the walls of the chambers of the radiological organ volumes intended to contain the dosimetry gels, a structure to hold the chambers together and ducts, for filling of the radiological organs, leading to outside the phantom.

For each chamber materialising the volume of a radiological organ, heed must be paid to two conditions:

The chamber must be held in position within the frame by means of a support to be printed at the same time as the organ chamber, at least two filling orifices must be made in the walls of the chamber connecting the chamber volume with the outside of the phantom to allow filling of the volume with the gel, at least one orifice being used as inlet for the dosimetry gel, at least one outlet orifice to allow evacuation of air as and when gel is filled without the formation of any air bubble.

Therefore, at the step to prepare planning for the frame of the physical phantom, for each organ of the model at least one gel inlet filling orifice, at least one air filling and outlet orifice and ducts for filling of the volumes of the radiological organs connected between the filling orifices and the outside of the phantom are respectively determined in terms of their positions, their diameters for the filling orifices, their positions, pathways and diameters for the filling ducts in relation to a triaxial geometric reference point related to the virtual frame.

For each radiological organ, the number of gel inlet filling orifices, the number of air filling and outlet orifices, the positions and diameters of the at least one gel inlet filling orifice and the at least one air filling and outlet orifice, and the pathways and diameters of the ducts for filling the radiological organ volumes connected between the filling orifices and the outside of the phantom are determined to allow filling of the radiological organ without any volume bubbles.

Additionally, and as a variant, the total number of filling orifices, the positions of the filling orifices and the pathways of the filling ducts, the smoothed forms of the radiological organ volumes are determined to avoid significant modification of radiation propagation towards the region to be treated as a function of the location of the region to be treated and of the entry angle of the radiation beam.

The filling system, formed by the filling ducts, can also act as supporting system forming part of the support of the radiological organs.

The total number of filling orifices, the positions of the filling orifices and the pathways of the filling ducts are determined so as to avoid any signification modification of radiation propagation towards the region to be treated as a function of the location of the region to be treated, of the entry angle of the radiation beam. This may involve having at least succinct knowledge of the entry angle of the radiation beams.

In the event of global exposure, the filling systems must be as small as possible.

Depending on their position and number, and the perturbation they cause to dose distribution in the phantom and thereby in the model in relation to reality, virtually determinable using a computing tool, an iterative computing process optimising the number thereof and the position of the ducts may require a review of organ surface smoothing or of the position of the filling orifices.

Once the architectural planning of the phantom frame is determined i.e. the plans integrating in one same structure the walls of the chambers provided with their filling orifices, the supporting system and the filling system, these plans are translated at the third step 8 to a 3D print control programme adapted for a given 3D printer, allowing effective obtaining of the material frame of the phantom.

At a fourth step 10, the material frame of the physical phantom without gels is formed using a 3D printing process using a 3D printer and the control programme prepared at the third step 8.

In the material frame of the gel-free physical phantom thus prepared, the cavities forming the organ volumes intended to be filled with dosimetry gels are filled with air and are each delimited by solid walls formed by the inks of the 3D printer selected to have properties equivalent to those of the biological tissues in terms of interaction with ionising radiation.

Next, at a fifth test step 12, the quality of the design and production of the empty physical phantom without gels is verified via mechanical and radiological performance tests.

The tested performances concern no phantom leakage, filling homogeneity and non-perturbation of dose distribution in the phantom caused by the filling orifices and ducts.

Non-leakage is sufficiently verified using a water filling test.

Filling homogeneity is verified through the absence of air bubbles.

Non-perturbation of dose distribution in the phantom caused by the filling orifices and ducts can be verified by visualising the pathway of future ionising radiation beams by means of light beams.

If at least one of the tests fails, the anomalies and critical points of the phantom are identified and translated into additional requirements for design of the phantom at a sixth step 14 to define additional constraints, and the second, third, fourth, fifth steps 6, 8, 10, 12 are once again carried out.

If the mechanical and radiological performance tests are successfully passed, then at a seventh step 16 each chamber of the phantom structure associated with a radiological organ is filled with a dosimetry gel having physical characteristics very close to the class of chemical compositions and densities of the radiological organ.

Preferably, filling of the phantom is performed in the liquid phase for each of the gels, and the gels are left to gel in the cavities until they reach the gel state properly so called, the gelling time being a function of the total mass of the gel contained in the phantom.

The filling of the internal volumes of the chambers is ensured by means of lines connecting the chamber to the outside of the empty phantom.

At the filling step 16, one or more dosimetry gels e.g. a Fricke gel or polymer gel are used. Preferably, the characteristics of these gels are close to the chemical compositions and densities of the different organs they simulate.

FIG. 2 illustrates a method 102 for the experimental determination of the volume distribution of radiation doses received by a phantom, representing the dose distribution which would be received by a biological organism placed under the same predetermined irradiating conditions, the method comprising a first step 104 to provide a radiometric physical phantom prepared according to the production method 2 in FIG. 1 or one of more variants thereof.

The experimental determination method 102 also comprises second and third steps 106 and 108 successively performed after the providing step 104 of the physical phantom.

At the second step 106, the physical phantom provided at the first providing step 102 is irradiated under the predetermined irradiating conditions which governed the design and preparation of the physical phantom provided, and which are identical to those to which a patient would be or has been subjected, for example via radiotherapeutic irradiation means such as a medical linear accelerator (LINAC) or any radiation installation for diagnostic purposes or any installation reproducing the conditions of an occurred irradiation accident.

The radiation used is ionising radiation e.g. photons, electrons, protons and heavy nuclei.

At the third step 108, a physical parameter of the irradiated gels is read out 110 in situ in the physical phantom, by placing the physical phantom filled with irradiated gels in imaging apparatus, and the read-out values of the physical parameter are encoded 112 in raw read-out data form. The imaging apparatus is apparatus using an optical transmission method for example, or Nuclear Magnetic Resonance NMR imaging apparatus.

The raw read-out data represent a read physical parameter e.g. optical density, relaxation time.

At the same third step 108, the raw read-out data are processed 114 to determine an image of the three-dimensional distribution of radiation doses received in the part or all of the biological organism.

The step to process read-out data 114 comprises the sub-steps 116, 118 whereby, on the basis of dosimetric calibration of the gels, the raw read-out data is translated into terms of absorbed doses in three-dimensional distribution, and the data translated into terms of absorbed doses are grouped together 118 to create particular images included in the group formed by two-dimensional sections along a predetermined sectional plane, three-dimensional « isodose » surface images, images proposed by the radiotherapy treatment planning software.

This dose distribution is compared with that provided by the radiotherapy treatment planning system or any other means to determine 3D distribution or computerised reconstitution of an accident. Comparison of the two distributions allows validation accordingly of the treatment modalities before actually irradiating a patient, or verification of the circumstances of the accident, and provides access to information useful for diagnosis and treatment.

In FIG. 3, a schematic solely illustrative radiological model 202 is shown in the form of a first global overhead view 204 and a second sectional view 206 of the radiological model 202 along a median plane 208 of section III-III perpendicular to the overhead view 204.

The radiological model comprises a medium 210 corresponding to a gel having equivalent characteristics on average to those of the non-identified organs contained in a parallelepiped 212; radiological organs 222, 224, 226, 228, 230, here a total number of five being identified within this same parallelepiped 212.

The volumes of the radiological organs 222, 224, 226 here are simplified as spheres of different radii, whilst the volumes of radiological organs 228 and 230 are respectively an elongate cylinder along an axis of vertical orientation in the sectional view 206, and a flattened disc in a plane perpendicular to the sectional plane 208, the cylinder and the disc having softened outlines.

The radiological organ 228 is formed of a first class of radiological material corresponding to a first hatch pattern 232, whilst the radiological organs 222, 230 are formed of a second class of radiological material corresponding to a second hatch pattern 234.

The radiological organs 222, 226, 230 are formed of a third class of radiological material corresponding to a third hatch pattern 236.

FIG. 4 is a sectional view of a frame 252 of a physical phantom obtained after 3D printing. The frame 252 of the physical phantom was obtained from the radiological model 202 in FIG. 3 following the steps in FIG. 1.

The frame 252 of the physical phantom comprises empty chambers 302, 304, 306, 308, 310, respectively defined by the volumes of the radiological organs in FIG. 3, and respectively delimited by walls 312, 314, 316, 318, 320 formed of one or more curable 3D printing inks transparent to radiation if the thickness thereof is sufficiently fine, or having interaction characteristics with ionising radiation similar to those of the simulated tissues or those of the gels confined therein.

Each chamber 302; 304; 306; 308; 310 here is provided on its wall with a gel inlet filling orifice and an air filling and evacuation orifice respectively connected to filling ducts 332, 333; 334, 335; 336, 337; 338, 339; 340, 341 leading to outside the frame 252 and connected to a supporting structure 342 to hold the chambers together.

The positions and diameters of the filling orifices, the diameters and pathways of the filling ducts 332, 333; 334, 335; 336, 337; 338, 339; 340, 341 are configured to allow the filling of each chamber 302; 304; 306; 308; 310 with its associated gel without the formation of volume bubbles.

The positions and diameters of the filling orifices, the diameters and pathways of the filling ducts 332, 333; 334, 335; 336, 337; 338, 339; 340, 341 are also configured to prevent the ducts from perturbing the expected dose distribution in the region of the phantom corresponding to the region to be treated of the biological organism as a function of the location of the region to be treated and the entry angle of the radiation beam. Here, the region to be treated is assumed to be located in the upper left part of the phantom in FIG. 4 before filling with the gels 252, and the radiation beam is directed along arrow 343. The filling orifices and ducts are therefore arranged here on the right side in FIG. 4. The routing of the ducts here is simple but it could be more complex in other cases.

It is to be noted that here the filling system, formed by the filling ducts, contributes towards holding the chambers together in addition to the action of other supporting structures 344, 346, 348.

As a variant, the filling system and the supporting system are separate.

In FIG. 5, a physical phantom 353 filled with non-irradiated dosimetric gels, obtained on completion of the production method in FIG. 1, comprises the frame 252 of the phantom in FIG. 4 wherein the chambers 302, 304, 306, 308, 310 are filled with their dosimetric gels having densities and chemical compositions corresponding to the classes of the radiological organs of the radiological model in FIG. 3.

Here the chamber 308 is filled with a first gel 362 corresponding to the first radiological class, the chambers 302, 306, 310 are filled with a second gel 364 corresponding to the second radiological class, and chamber 304 is filled with a third gel 366 corresponding to the third radiological class.

FIG. 6 illustrates a system 402 to produce the radiometric physical phantom of FIG. 5 using the phantom production method 2 in FIG. 1.

The production system 402, delimited by edging in dotted lines in FIG. 6, comprises means 404 to provide one or more three-dimensional anatomical images of the tissues of the biological organism in terms of chemical compositions and densities, an electronic computer 406, 3D printer 408, at least two different dosimetric gels, here three gels 362, 364, 366, and means 368 for filling the empty phantom 352 with the dosimetric gels 362, 364, 366.

The electronic computer 406 is configured to determine a three-dimensional 3D radiological model representing radiation absorption and diffusion in the biological organism, by grouping together in radiological organs those tissues that are adjacent and have close chemical compositions and densities. Each radiological organ occupies a radiological organ volume delimited by a corresponding enveloping surface. The radiological volume is equal to, or close to via smoothing of its contours, the sum of the volumes of the tissues grouped together within the radiological organ. Each radiological organ is characterized by a class of close chemical compositions and densities.

The electronic computer 406 is also configured so that at step 8 in FIG. 1, on the basis of the three-dimensional radiological model, it can determine the plans for a material frame of a physical phantom being composed of all the enveloping surfaces of the radiological organs or walls of organ chambers, held in relative positions, all the filling ducts, all the supporting elements, and then translate the frame plans into commands for production thereof by a predetermined 3D printer.

The 3D printer 408 is configured to produce the material frame 252 of the phantom non-filled with dosimetric gels, by means of printing inks having interaction properties with ionising radiation close to those of the gels and biological tissues they represent.

The 3D printers currently available allow the printing of a volume 60×60×60 cm3, said volume being sufficient to represent all the parts of a patient. The walls of the radiological volumes representing the organs can be in plastic without causing any notable perturbation to measurement, but compositions close to those of the tissues can be used when available.

The dosimetric gels are each intended to fill a different radiological chamber associated with a different radiological organ in terms of class of chemical compositions and densities. Dosimetric gels are substances having a gelatinous texture at ambient temperature and contain a species the nature of which is modified during radiation, e.g. ferrous iron which is converted to ferric iron for a Fricke gel, or a phenomenon of polymerisation for a polymer gel. Such gels are described for example in the article by L. J. Scheiner: « Review of Fricke gel dosimeters » published in Journal of Physics: Conference Series3 (2004) 9-21.

In FIG. 7, a system for experimental determination 502 of the volume distribution of radiation doses received by the phantom in FIG. 5 produced by the production system in FIG. 6 and implementing the experimental determination method 102 in FIG. 2, comprises a system 402 to produce a radiometric physical phantom filled with dosimetric gels such as described in FIG. 6, means 504 to irradiate the physical phantom with radiation under predetermined irradiating conditions, means 506 to read out a physical parameter of the gels in situ in the phantom, means 508 to encode the read-out physical parameter in the form of raw read-out data, and means 510 to process the raw read-out data.

The reader means 506 are used by placing the physical phantom filled with irradiated gels 512 in imaging apparatus using an optical transmission method for example, or in NMR imaging apparatus.

The means 510 to process the raw read-out data are configured to determine an image of the three-dimensional distribution of the radiation doses received in the part or all of the biological organism.

Two examples of application of the invention are described below.

According to a first example concerning radiotherapy, when planning treatment, a series of diagnostic images is obtained using a conventional technique such as scanning or NMR. These images are used by the medical team to delimit the contours of tumours and are then inserted in treatment planning programmes which generate a treatment plan defining the quality, beam collimation, the number and incidence of radiation beams directed onto the patient. In this case, the performing of treatment not on the patient but on the physical phantom accurately representing the patient, allows a comparison to be made between the dose distribution such as planned and the distribution actually administrated to the phantom. This provides an a priori validation tool of the treatment. It is also possible a posteriori to reproduce a treatment that has been administered for examination thereof. In both cases, measurement gives access to information on dose distribution outside volumes generally investigated by planning software. Such information can prove to be of high interest for studies on second cancers which could be radio-induced.

According to a second example concerning the reconstitution of a radiological accident, the treatment of irradiated persons after the radiological accident is dependent on the manner in which they were irradiated i.e. the dose distribution in the different organs. This dose distribution can be computed using accident reconstitution software, and even estimated from measurement in standard phantoms. The measurement of this dose distribution in a realistic anthropomorphic phantom representing the true internal and external « geometry » of the patient is then compared with the computed measurement. This comparison allows validation of computing results, and subsequently to verify the circumstances of the accident, thereby providing access to information useful for diagnosis and treatment.

In these two examples, the use of anthropomorphic phantoms such as proposed by the invention and representing the particularities of a patient, when associated with measuring means evaluating dose distribution in a patient in three dimensions and with a single measurement, e.g. a scanner or NMR station, allows more precise and more rapid validation.

The phantoms of the invention will most often be anthropomorphic phantoms and can be used for any type of external radiotherapy: RCMI/IMRT (and all rotational irradiation—Tomotherapy, VMAT, Rapidarc . . . ); stereotaxy; proton/hadron therapy; brachytherapy.

This use comes within the scope of a quality assurance process (experimental verification of treatments) or a posteriori studies on risks of « second cancer ». More generally, to include cases of accident reconstitution, these phantoms are useful in all areas where knowledge of dose distribution in a patient is necessary a priori or a posteriori: testing and validation of radiotherapy treatments, testing and validation of exposure to ionising radiation for diagnostic purposes, a posteriori study on treatment already administered, and radiological accident reconstitution.

The invention claimed is:

1. A method to produce a radiometric physical phantom of a biological organism for the experimental determination, under predetermined irradiating conditions, of the volume distribution of radiation doses received by the phantom, representing the dose distribution which would be received by the biological organism placed under the same irradiating conditions, the biological organism having at least two volumes of biological tissues with distinctly different chemical compositions and densities, the production method comprising the steps of:

from one or more three-dimensional anatomical images of the tissues in terms of chemical composition and density, determining a three-dimensional radiological model representing radiation absorption and diffusion inside the biological organism, by grouping together in radiological organs those tissues that are adjacent and have close chemical compositions and densities;

each radiological organ geometrically occupying in space a radiological volume equal to, or close to via smoothing of its enveloping contours, the sum of the volumes of all the tissues grouped together within the same radiological organ, and being characterized by a radiological class identifying the range of close chemical compositions and densities of the tissues grouped together in the same radiological organ; then from the radiological model, by means of 3D printing, forming a material frame of the physical phantom by reproducing each radiological volume via a chamber filled with air and delimited by a wall, the wall being formed by 3D printing ink; and then filling each chamber of the material frame of the phantom, associated with a radiological organ, with a dosimetric gel having physical characteristics close to or identical to those of the class of chemical composition and densities of the radiological organ.

2. The method to produce a radiometric physical phantom according to claim 1, wherein when determining the radiological model:

for each group of biological tissues in one same radiological organ:

an intermediate radiological volume is first determined as being equal to the sum of the volumes of the tissues grouped together in the radiological organ, then the radiological volume of the radiological organ is determined by smoothing the contours of the intermediate radiological volume to limit anfractuosities and to facilitate filling with the dosimetric gel.

3. The method to produce a radiometric physical phantom according to claim 2, further comprising a step to prepare software planning for production of the material frame of the phantom and translation of these plans into a control programme for 3D printing of the frame, inserted between the step of determining the radiological model and the step of forming the material frame of the physical phantom by 3D printing, and during said preparation step:

for each chamber associated with a radiological organ, the number of gel inlet filling orifices, the number of air filling and outlet orifices, the positions and diameters of the gel inlet filling orifice(s) and of the air filling and outlet orifice(s) as well as the pathways and diameters of the chamber filling ducts connected between the filling orifices and the outside of the phantom, are determined so as to allow filling of the radiological organ without any volume bubbles.

4. The method to produce a radiometric physical phantom according to claim 3, wherein the total number of filling orifices, the positions of the filling orifices and the pathways of the filling ducts for all the chambers are determined so as not to hamper propagation of radiation towards a region to be treated as a function of the location of the region to be treated and/or of the entry angle of the radiation beam.

5. The method to produce a radiometric phantom according to claim 4, wherein the smoothed forms of the volumes of the chambers are also determined so as not to hamper propagation of radiation towards a region to be treated as a function of the location of the region to be treated and/or of the entry angle of the radiation beam.

6. The method to produce a radiometric phantom according to claim 1, wherein the dosimetric gels are included in the group formed by Fricke gels and polymer gels.

7. A method for experimental determination of the volume distribution of radiation doses received by a radiometric physical phantom representing a dose distribution which would be received by all or part of a biological organism placed under the same predetermined irradiating conditions, comprising the steps of:

providing a physical phantom filled with dosimetric gels and produced according to claim 1;

irradiating the physical phantom under the predetermined irradiating conditions;

carrying out reading of a physical parameter of the gels in situ in the phantom by placing the phantom filled with irradiated gels in imaging apparatus, for example using an optical transmission method or NMR imaging equipment, and encoding the parameter in the form of raw read-out data; and processing the raw read-out data to determine an image of the three-dimensional distribution of radiation doses received in all or part of the biological organism.

8. The method for experimental determination of the volume distribution of radiation doses received by a physical phantom according to claim 7, characterized in that the raw read-out data represent a read-out physical parameter included the group formed by optical density, relaxation time.

9. The method for experimental determination of the volume distribution of radiation doses received by a physical phantom according to claim 7, wherein the processing step of the read-out data comprises the steps of:

translating the raw read-out data into terms of absorbed doses; and grouping together the data translated into terms of absorbed doses to create particular images included in the group formed by two-dimensional cross-sections along a predetermined sectional plane, three-dimensional « isodose » surfaces, images proposed by radiotherapy treatment planning software.

10. The method for experimental determination of the volume distribution of radiation doses due to radiation received by a phantom according to claim 7, wherein the radiation is particle radiation included in the group formed by photons, electrons, protons, and heavy nuclei.

11. A radiometric physical phantom of a biological organism for experimental determination, under predetermined irradiating conditions, of the volume distribution of radiation doses received by the phantom representing the dose distribution which would be received by the biological organism placed under the same irradiating conditions, the biological organism having at least two volumes of biological tissues having distinctly differing chemical compositions and densities, characterized in that the physical phantom comprises:

at least two chambers, held in position within a supporting frame, delimited by respective walls formed of solid 3D printing ink transparent to radiation, and each filled with a different dosimetric gel;

the at least two chambers having different, separate radiological volumes, each radiological volume being identical to, or close to via smoothing of contours, the sum of the volumes of a complete group of grouped biological tissues of the biological organism that is radiologically imitated, said grouped tissues being adjacent and having close chemical compositions and densities; and the dosimetric gels filling said chambers each having physical characteristics close to the chemical compositions and densities of the grouped adjacent biological tissues, the sum of the volumes thereof being identical to, or close to via smoothing, the radiological volume of the chamber that is filled with the gel.

12. The radiometric phantom according to claim 11, wherein:

each chamber comprises at least one gel inlet filling orifice and at least one air filling and outlet orifice, and at least two filling ducts connected between the filling orifices and the outside of the phantom; and for each chamber, the number of gel inlet filling orifices, the number of air filling and outlet orifices, the positions and the diameters of the gel inlet filling orifices and of the air filling and outlet orifices, as well as the pathways and diameters of the chamber filling ducts, connected between the filling orifices and the outside of the phantom, are configured to allow the filling of the chamber at a predetermined rate without the creation of any volume bubbles.

13. A system to produce a radiometric physical phantom simulating the radiation absorption and diffusion properties of a biological organism, the biological organism having at least two volumes of biological tissues with distinctly differing chemical compositions and densities, the system comprising:

means to provide one or more three-dimensional anatomical images of the tissues in terms of chemical composition and density;

an electronic computer configured:

from one or more three-dimensional anatomical images of the tissues in terms of chemical composition and density, to determine a three-dimensional radiological model representing radiation absorption and diffusion inside the biological organism, by grouping together in radiological organs those tissues that are adjacent and have close chemical compositions and densities;

each radiological organ geometrically occupying in space a radiological volume equal to, or close to via smoothing of its enveloping contours, the sum of the volumes of all the tissues grouped together within the same radiological organ, and being characterized by a radiological class identifying the range of close chemical compositions and densities of the tissues grouped together in the same radiological organ; and from the three-dimensional radiological model, to determine the plans of a material frame of the phantom as being a set of chambers, ducts for filling the chambers with gel and supporting elements to hold the chambers in position together, then to translate the plans of the material frame into a 3D print control programme to be executed by a predetermined 3D printer, the predetermined 3D printer being configured to produce the material frame of the phantom non-filled with dosimetric gels, using 3D printing inks transparent to radiation;

at least two different dosimetric gels each intended to fill a different radiological chamber associated with a different radiological organ in terms of class of chemical composition and density; and means to fill the empty phantom with the at least two dosimetric gels.

14. The system to produce a radiometric physical phantom according to claim 13, wherein the electronic computer, for each group of biological tissues in a radiological organ, is configured to:

determine an intermediate radiological volume as being equal to the sum of the volumes of the tissues grouped together in the radiological organ; and determine the radiological volume of the radiological organ by smoothing the contours of the intermediate radiological volume to limit anfractuosities and to facilitate future filling with gel.

15. The system to produce a radiometric physical phantom according to claim 13, wherein the electronic computer, for each radiological organ, is configured to:

determine the number of gel inlet filling orifices, the number of air filling and outlet orifices, each position and diameter of the gel inlet filling orifices(s), each position and diameter of the air filling and outlet orifice(s), and the pathways and diameters of the filling ducts for the radiological organ volumes connected between the filling orifices and the outside of the phantom, so as to:

allow filling of the radiological organ without any volume bubbles.

16. The system to produce a radiometric physical phantom according to claim 15, wherein the electronic computer is configured to determine the total number of filling orifices, the positions of the filling orifices and the pathways of the filling ducts so that the ducts do not hamper propagation of radiation towards a region to be treated as a function of the location of the region to be treated and the entry angle of the radiation beam.

17. The system to produce a radiometric physical phantom according to claim 16, wherein the electronic computer is configured also to determine the smoothed forms of the volumes of the radiological organs so as to avoid significant modification of radiation propagation towards a region to be treated as a function of the location of the region to be treated and of the entry angle of the radiation beam.

18. A system for the experimental determination of the volume distribution of radiation doses received by a phantom representing a dose distribution which would be received by all or part of a biological organism placed under the same predetermined irradiating conditions, comprising:

a system to produce a radiometric physical phantom filled with dosimetric gels defined according to claim 13;

means to irradiate the physical phantom with radiation under predetermined irradiating conditions;

means to read a physical parameter of the gels in situ in the phantom when this phantom is filled with irradiated gels and placed in imaging apparatus using an optical transmission method for example, or in NMR imaging apparatus, and means for encoding the read-out physical parameter into raw read-out data;

means to process the raw read-out data to determine an image of the three-dimensional distribution of the radiation doses received in the biological organism.

* * * * *